United States Patent [19]

Feuer et al.

[11] 4,102,948
[45] Jul. 25, 1978

[54] ω-AMINOCARBOXYLIC ACID AMIDE PHOSPHATES

[75] Inventors: László Feuer; Árpád Furka; Ferenc Sebestyén; Anikó Horváth; Jolán Hercsel nee Szepespataki, all of Budapest, Hungary

[73] Assignee: Chinoin Gyogyszer es Vegyeszeti Termekek Gyara Rt., Budapest, Hungary

[21] Appl. No.: 792,917

[22] Filed: May 2, 1977

[30] Foreign Application Priority Data

May 6, 1976 [HU] Hungary ............... CI 1662

[51] Int. Cl.² ............ C07F 9/09; A01N 9/36
[52] U.S. Cl. .................... 260/944; 260/968; 424/211
[58] Field of Search ........................ 260/944

[56] References Cited

U.S. PATENT DOCUMENTS 2,229,744  1/1941  Kern ................. 260/944 X

FOREIGN PATENT DOCUMENTS 2,518,160  11/1975  Fed. Rep. of Germany ....... 260/944

Primary Examiner—Anton H. Sutto
Attorney, Agent, or Firm—Karl F. Ross

[57] ABSTRACT

Compounds of the formula:

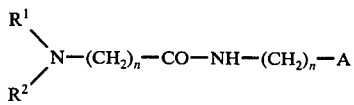

or pharmaceutically acceptable salts thereof, wherein:
A is $-OPO(OH)_2$;
$R^1$ is hydrogen, acetyl or benzoyl;
$R^2$ is hydrogen; and
$n$ is 2 or 3 with the ability to decrease blood sugar are disclosed.

8 Claims, No Drawings

ω-AMINOCARBOXYLIC ACID AMIDE PHOSPHATES

This invention relates to novel ω-aminocarboxylic acid amides having the formula (I)

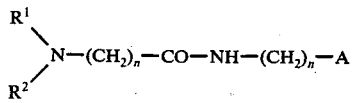
$$R^1\!\!\diagdown\!\!\!\!\!\!\!\!\!\!_{R^2\diagup}\!\!N-(CH_2)_n-CO-NH-(CH_2)_n-A \quad (I)$$

wherein
A is a group of the formula -OPO(OH)$_2$,
$R^1$ is hydrogen, acetyl benzoyl,
$R^2$ is hydrogen and
n is equal to 2 or 3,
and salts of the above compounds. The invention relates also to a process for the preparation of such ω-aminocarboxylic acid amides.

The preferred species according to the invention include:

gamma-aminobutyryl-ethanolamine phosphate;
N-acetyl-gamma-aminobutyryl-ethanolamine phosphate;
N-benzoyl-gamma-aminobutyryl-ethanolamine phosphate;
gamma-aminobutyryl-propanolamine phosphate;
beta-alanyl-ethanolamine phosphate; and
beta-alanyl-propanolamine phosphate;

or a pharmaceutically acceptable salt of any of the above.

The novel compounds according to the invention possess valuable therapeutical effects or can be used as intermediates in the synthesis of compounds with valuable biological or pharmacological activities.

With respect to their pharmacological activities, γ-amino-butyryl-ethanolamine phosphate is a particularly interesting representative of the novel compounds according to the invention. These substances, even when administered in very low concentrations (some micrograms per kg body weight), significantly decrease the blood sugar level of rats, increase the vitamin A level of the serum, and enhance the incorporation of labelled sulfate ions into the lung tissues of chicken embryos.

A common structural characteristic of the novel compounds having the general formula (I) is that they are amido derivatives of β- or γ-aminocarboxylic acids having optionally a substituent on the amino group, wherein the alkyl side chain of the amide-forming primary alkylamine moiety contains a strongly acidic group in position β or γ.

The new compounds according to the invention can be prepared far more simply and easily than the structurally related α-amino-dicarboxylic acid amides, since in this instance the carboxy group in position α need not be protected.

The novel compounds of the formula (I) and their salts can be prepared according to the invention as follows:

a) when a compound of the general formula (I) containing an unsubstituted primary amino group is to be prepared, the $R^3$ and/or $R^4$ protecting groups of a compound having the formula (II),

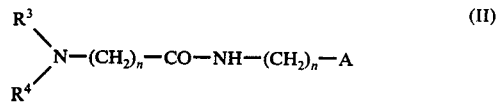
$$R^3\!\!\diagdown\!\!\!\!\!\!\!\!\!\!_{R^4\diagup}\!\!N-(CH_2)_n-CO-NH-(CH_2)_n-A \quad (II)$$

wherein
n and A are as defined above and
$R^3$ represents an aralkyl, formyl, trifluoroacetyl, p-toluenesulfonyl or carbonyl group or a group of the general formula $R^{12}$—O—CO— (wherein $R^{12}$ is a $C_{1-4}$ alkyl, cycloalkyl, aralkyl, substituted aralkyl, aryl or substituted aryl group) and
$R^4$ is hydrogen or carbonyl group, with the proviso that when
$R^3$ and $R^4$ each stand for carbonyl, the two carbonyl groups form a ring through an intervening o-phenylene group, are split off by acidolysis, hydrogenolysis, treatment with a dilute ammonium hydroxide solution, treatment with sodium amide or treatment with hydrazine; or (b) when a compound of the formula (I) containing an unsubstituted primary amino group is to be prepared, a compound of the formula (VI),

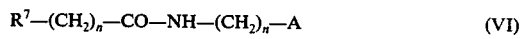
$$R^7-(CH_2)_n-CO-NH-(CH_2)_n-A \quad (VI)$$

wherein n and A are as defined above and $R^7$ stands for halogen, nitro, hydrazino, hydroxylamino, p-toluenesulfonyloxy, arylazo, substituted arylazo, monoarylhydrazino or diarylhydrazino group, is reduced or reacted with ammonia; or (c) when a compound of the formula (I) containing an unsubstituted primary amino group is to be prepared, a compound of the formula (VII),

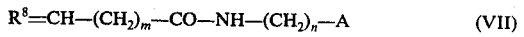
$$R^8\!\!=\!\!CH-(CH_2)_m-CO-NH-(CH_2)_n-A \quad (VII)$$

wherein n and A are as defined above, m is equal to 1 or 2, and $R^8$ is oxygen, oximino group, imino group or a group of the general formula =N—N-H—$R^{13}$, and in this latter formula $R^{13}$ stands for hydrogen or an aryl group, is reduced or reacted with ammonia and potassium cyanide, and the resulting compound is hydrogenated, or it is reacted with α-methyl-benzylamine and the resulting compound is hydrogenated; or (d) a compound of the formula (VIII),

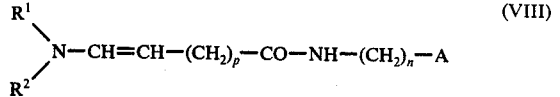
$$R^1\!\!\diagdown\!\!\!\!\!\!\!\!\!\!_{R^2\diagup}\!\!N-CH=CH-(CH_2)_p-CO-NH-(CH_2)_n-A \quad (VIII)$$

wherein $R^1$, $R^2$, n and A are as defined above and p is equal to zero or one, is hydrogenated; or (e) when a compound of the general formula (I) containing γ-aminobutyric acid units to be prepared, a compound of the formula (IX),

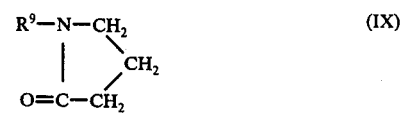

wherein $R^9$ is hydrogen a $C_{1-4}$ alkyl, aryl, substituted aryl, aralkyl, acyl, arylsulfonyl group or a group of the general formula $R^{12}$—O—CO—, and in this latter formula $R^{12}$ stands for a $C_{1-4}$ alkyl, cycloalkyl, aralkyl, substituted aralkyl, aryl or substituted aryl group, is reacted with a compound of the formula (X)

$$H_2N-(CH_2)_n-A \qquad (X)$$

wherein n and A are as defined above, or with a salt of said compound; or (f) when a compound of the general formula (I) containing a protecting group on the amino group is to be prepared, a compound of the formula (XIII),

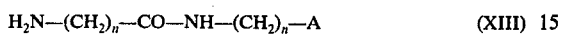

$$H_2N-(CH_2)_n-CO-NH-(CH_2)_n-A \qquad (XIII)$$

wherein n and A are as defined above, is acylated; and, if desired, a compound of the formula (I) is converted into its salt, or a salt of a compound having the formula (I) is converted into the free base.

According to methods (b) and (c) a carboxylic amide containing a substituent other than amino group in position $\beta$ or $\gamma$ is converted into the corresponding $\beta$- or $\gamma$-amino derivative. As starting compounds amides or $\beta$- or $\gamma$-nitro-, arylazo-, hydrazo-, arylhydrazo-, hydroxylamino-, oximino- or iminocarboxylic acids, furthermore amides of $\beta$- or $\gamma$-ketocarboxylic acid hydrazones can be applied. These compounds can be converted into the desired end-products of the general formula (I) by reduction, preferably by catalytic hydrogenation. When a $\beta$- or $\gamma$-halo- or $\beta$- or $\gamma$-(p-toluenesulfonyloxy)-carboxylic acid amide is applied as starting substance, the desired $\beta$- or $\gamma$-amino compounds of the formula (I) can be prepared by amine substitution. The amino group can be introduced into the molecule by methods known per se. Similarly, the corresponding $\beta$- or $\gamma$-ketocarboxylic acid amides can be converted into the $\beta$- or $\gamma$-amino compounds of the formula (I) by methods known per se, e.g. by reacting the keto derivatives with potassium cyanide in the presence of ammonium hydroxide and hydrogenating the resulting compound in the presence of cobalt chloride (Bull. Chem. Soc. Japan 36, 763 /1963/).

When a compound containing a double bond in the $\beta$- or $\gamma$-aminocarboxylic acid moiety is used as the starting substance, this can be converted into the corresponding derivative of the formula (I) by hydrogenation (see method g).

End-products of the formula (I) can also be prepared by method (e). In this instance when e.g. pyrrolid-1-one is reacted with another amine containing a strongly acidic functional group, or with an alkali metal or tertiary amine salt of the above compounds, the lactam ring splits off and a $\beta$- or $\gamma$-amide of the formula (I) is formed.

Those compounds of the formula (I), wherein a substituent is attached to the amino group, can be prepared from the corresponding unsubstituted amino derivatives. According to method (f) the free amino compounds are acylated in a manner known per se to form e.g. the corresponding acetyl, benzoyl, p-toluenesulfonyl, etc. compounds.

The pharmacological properties of the novel compounds according to the invention were investigated by the following tests:

Effects of γ-Aminobutyryl-Cholamine Phosphate Exerted on the Blood Sugar Level The tests were performed on groups each consisting of 20 rats. The blood sugar level values were measured after 18 hours of starvation. The compounds under study were administered for 4 days in the form of a solution in daily oral dosages of 1 μg/kg body weight. The following results were observed:

control: 106 mg%
γ-aminobutyryl-cholamine phosphate: 95 mg%
γ-aminobutyryl-taurine: 92 mg%
Significance level: $P < 0.05$ for both cases.

Effects of γ-Aminobutyryl-Cholamine Phosphate Exerted on the Serum Vitamin A Level The tests were performed on male Wistar rats weighing 200 g. Groups each consisting of 20 rats were applied in the tests. The test period lasted 6 days. The results are summarized in Table 1.

Table 1

| Dosage μg/200 g body wt. | Vitamin A level, μg% | Dosage μg/200 g body wt. | Vitamin A level, μg% |
|---|---|---|---|
| 0 | 9.0 | 0.1 | 16.6* |
| 5 | 11.5* | 0.05 | 15.2* |
| 1 | 12.5* | 0.01 | 14.8* |
| 0.3 | 13.5* | 0.005 | 14.8* |

*Significance level: $P < 0.01$

Effects of γ-Aminobutyryl-Cholamine Phosphate on Blood Silicon Level

The tests were performed on inbred male rabbits weighing 2.5 to 3 kg. The compound under study was administered orally to the animals in the daily dosages indicated in Table 2 below. The silicon content of the blood was determined according to the method of Gaubatz (Klin. Wschrft. 14, 1753, 1935) from blood samples, 5 ml in volume, taken from the ear vein. The results observed are summarized in Table 2.

Table 2

| Dosage | Silicon level, mg/g of blood | | | | | |
|---|---|---|---|---|---|---|
| | 0 hours | 5th day | 7th day | 13th day | 20th day | 40th day |
| 0 (control) | 0.100 ±0.005 | 0.098 ±0.011 | 0.120 ±0.017 | 0.122 ±0.016 | 0.130 ±0.011 | 0.153 ±0.016 |
| 5 μg/day | 0.090 ±0.003 | 0.156 ±0.010 | 0.154 ±0.006 | 0.184 ±0.005* | 0.305 ±0.010** | 0.336 ±0.011** |
| 10 μg/day | 0.105 ±0.005 | 0.174 ±0.004 | 0.170 ±0.004 | 0.200 ±0.011* | 0.368 ±0.115** | 0.359 ±0.013** |

Significance levels: *$P < 0.01$ **$P < 0.001$

The results are significant on the $P < 0.01$ level from the 13th day on, and on the $P < 0.001$ level from the 20th day on.

Joint Effects on γ-Aminobutyrl-Cholamine Phosphate and Vitamin A in the Implantation Cotton Granuloma Test The tests were performed on male Sprague-Dawley rats weighing 110 to 120 g. The granuloma formation was tested according to the method of Lee et al. (Pharm. Sci. 62, 895 /1973/). The cotton tampons, implanted subcutaneously into the dorsolateral region, were removed after 10 days. The tampons were dried at 65° C until constant weight and then weighed. The results are listed in Table 3.

Table 3

| Group No. | Vitamin A[x] local, mg | Active agent local μg | Active agent oral μg/day | Weight of the dry granuloma mg |
|---|---|---|---|---|
| I. (control) | — | — | — | 50 ± 1.3 |
| II. (solvent) | — | — | — | 51 ± 3.0 |
| III. | 2 | — | — | 62 ± 22.1 |
| IV. | 2 | 0.1 | — | 63 ± 2.2 |
| V. | — | — | 0.1 | 75 ± 2.4 |
| VI. | 2 | — | 0.1 | 92 ± 4.0 |

The significance levels are as follows:
between groups II and III: $P < 0.05$
between groups II and V: $P < 0.001$
between groups V and VI: $P < 0.01$ The invention is elucidated in more detail by the aid of the following non-limiting Examples.

EXAMPLE 1

3.94 g (11 mmoles) of N-carbobenzoxy-γ-aminobutyric acid p-nitrophenylester (J. org. Chem. 27, 684 1962) are dissolved in 75 ml of absolute pyridine, and the solution is cooled to 0° C. A solution of 1.25 g (10 mmoles) of taurine in 10 ml of water is added to the above solution under stirring and without further cooling, and then 1.4 ml (10 mmoles) of triethylamine are added. The reaction mixture is allowed to stand at room temperature for 72 hours, and then it is evaporated in vacuo at 35° C. The residue is dissolved in 10 ml of water, the solution is acidified with concentrated hydrochloric acid, and the acidic mixture is extracted in a continuous extractor for 8 hours with ether in order to remove p-nitro-phenol. The aqueous phase is evaporated in vacuo. The residue is dissolved in 10 ml of water, and the solution is poured onto a chromatographic column (20 × 2.2 cm) filled with Dowex 50×2 resin in the H[30] form. The column is eluted with water. 150 ml of the effluent are collected. This solution, now free of triethylamine, is evaporated in vacuo at 35° C. The residue is dried in a desiccator over phosphorous pentoxide. 3.23 g (94%) of N-carbobenzoxy-γ-aminobutyryl-taurine are obtained.

EXAMPLE 2

10 ml of glacial acetic acid and 15 ml of a 3,3 molar hydrogen bromide solution in glacial acetic acid are added to 3.23 g of N-carbobenzoxy-γ-aminobutyryl-taurine, prepared as described in Example 1. The mixture is allowed to taurine) of at room temperature for 2 hours, and then evaporated in vacuo at 35° C. The oily residue is triturated several times with ether, and the etheral phase is decanted. The residue is dried in a desiccator over solid potassium hydroxide. The obtained oily residue is dissolved in 2 ml of water and crystallized by the addition of 20 ml of acetone. The crude product is recrystallized from a 1:10 mixture of water and acetone to obtain 1.89 g (90 %, calculated for the starting taurine) of γ-amino-butyryl-taurine.

EXAMPLE 3

3.94 g (11 mmoles) of N-carbobenzoxy-aminobutyric acid p-nitrophenyl ester are dissolved in 60 ml of absolute pyridine. The solution is cooled to 0° C, then the cooling bath is removed, and a solution of 1.41 g (10 mmoles) of ethanolamine phosphate in 20 ml of water is added dropwise to the stirred mixture. Thereafter 2.8 ml (20 mmoles) of triethylamine are added to the solution, and the mixture is allowed to stand at room temperature for 72 hours. The solution is evaporated in vacuo at 35° C. The oily residue is diluted with 10 ml of water, the aqueous solution is acidified with concentrated hydrochloric acid, and the acidic mixture is extracted continuously with ether for 8 hours. The aqueous phase is evaporated in vacuo. The oily residue is dissolved in 20 ml of distilled water, and the solution is poured onto a chromatographic column (36×2.2 cm) filled with Dowex 50×2 resin in the H+ form.

EXAMPLE 4

The protecting group of 3.13 g of N-carbobenzoxy-γ-aminobutyryl-ethanolamine phosphate is split off as described in Example 2. The crude product is recrystallized from a 1:9 mixture of water and methanol to obtain 1.83 g (81 %) of γ-aminobutyryl-ethanolamine phosphate; m.p.: 207° C.

Characteristic bands appearing in the IR absorption spectrum (KBr): 3295 (amide =NH), 3200–2000 ($NH_3^+OH^-$). 1642 (amide =CO), 1558 (amide =NH), 1145 (P=O in H-bond), 1045 (broad; asymmetric P—O—C—), 957 (symmetric P—O—C—) $cm^{-1}$.

Analysis: Calculated for $C_6H_{15}N_2O_5P$ (226.182): C, 31.86%; H, 6.68 %; N, 12.39 %; P, 13.70 %. Found: C, 31.50 %; H, 6.97 %; N, 12.04%; P, 13.40%.

What we claim is:
1. A compound of the formula:

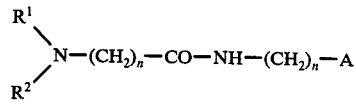

or a pharmaceutically acceptable salt thereof, wherein:
A is $-OPO(OH)_2$;
$R^1$ is hydrogen, acetyl or benzoyl;
$R^2$ is hydrogen; and
$n$ is 2 or 3.

2. A compound selected from the group consisting of: γ-aminobutyryl-ethanolamine phosphate;
N-acetyl-γ-aminobutyryl-ethanolamine phosphate;
N-benzoyl-γ-aminobutyryl-ethanolamine phosphate;
γ-aminobutyryl-propanolamine phosphate;
β-alanyl-ethanolamine phosphate; and
β-alanyl-propanolamine phosphate, or a pharmaceutically acceptable salt thereof.

3. The compound defined in claim 2 which is γ-aminobutyryl-ethanolamine phosphate.

4. The compound defined in claim 2 which is N-acetyl-γ-aminobutyryl-ethanolamine phosphate.

5. The compound defined in claim 2 which is N-benzoyl-γ-aminobutyryl-ethanolamine phosphate.

6. The compound defined in claim 2 which is γ-aminobutyryl-propanolamine phosphate.

7. The compound defined in claim 2 which is β-alanyl-ethanolamine phosphate.

8. The compound defined in claim 2 which is β-alanyl-propanolamine phosphate.

* * * * *